(12) United States Patent
Simpson

(10) Patent No.: US 11,305,052 B2
(45) Date of Patent: Apr. 19, 2022

(54) SUCTION-BASED MEDICAL DRESSING AND METHOD OF DERMAL IRRIGATION

(71) Applicant: Steven Simpson, Safety Harbor, FL (US)

(72) Inventor: Steven Simpson, Safety Harbor, FL (US)

( * ) Notice: Subject to any disclaimer, the term of this patent is extended or adjusted under 35 U.S.C. 154(b) by 309 days.

(21) Appl. No.: 16/377,216

(22) Filed: Apr. 7, 2019

(65) Prior Publication Data

US 2020/0316272 A1 Oct. 8, 2020

(51) Int. Cl.
| | |
|---|---|
| *A61M 1/00* | (2006.01) |
| *A61F 13/02* | (2006.01) |
| *A61F 13/00* | (2006.01) |
| *A61F 15/00* | (2006.01) |

(52) U.S. Cl.
CPC ....... *A61M 1/964* (2021.05); *A61F 13/00068* (2013.01); *A61F 13/023* (2013.01); *A61M 1/0023* (2013.01); *A61F 15/008* (2013.01); *A61F 2013/00174* (2013.01)

(58) Field of Classification Search
CPC ............ A61M 1/90; A61M 2205/3331; A61M 2205/50; A61M 1/73; A61M 2205/3379; A61F 13/00068; A61F 13/0216; A61F 2013/0094
See application file for complete search history.

(56) References Cited

U.S. PATENT DOCUMENTS

| | | | |
|---|---|---|---|
| 5,215,539 A | 6/1993 | Schoolman | |
| 6,960,181 B2 | 11/2005 | Stevens | |
| 7,816,577 B2 | 10/2010 | Aali | |
| 8,067,662 B2 | 11/2011 | Aali et al. | |
| 8,409,159 B2 | 4/2013 | Hu et al. | |
| 8,586,818 B2 | 11/2013 | Aali | |
| 8,858,516 B2 | 10/2014 | Hu et al. | |
| 9,889,241 B2 | 2/2018 | Vess et al. | |
| 2007/0219497 A1* | 9/2007 | Johnson | A61M 37/00 604/131 |
| 2008/0119802 A1* | 5/2008 | Riesinger | A61M 27/00 604/313 |
| 2008/0208171 A1* | 8/2008 | Argenta | A61M 1/90 604/540 |

(Continued)

*Primary Examiner* — Andrew J Mensh
*Assistant Examiner* — Nhu Q. Tran
(74) *Attorney, Agent, or Firm* — Mark C. Johnson; Johnson Dalal

(57) ABSTRACT

A suction-based medical dressing assembly and method of dermal irrigation provides a flexible tube that is fluidly coupled to at least two bifurcated tube portions defined by a plurality of apertures. The tube has a proximal end opening for discharging ambient fluid. The length of the bifurcated tube portions is surrounded by an absorbent gauze material covered substantially with an occlusive sheet material, and having an adhesive strip thereon. A vacuum assembly creates a negative pressure in the tubes. The ambient fluid is absorbed by the absorbent material, and the negative pressure sucks the fluid through the apertures in the bifurcated tube portions for discharge through the opening in the tube. In operation, a patient applies the adhesive side of the occlusive device to the skin where liquid removal is desired and activates the vacuum-inducing source, thereby causing fluid runoff from the patient to be effectively removed for disposal.

20 Claims, 14 Drawing Sheets

(56) References Cited

U.S. PATENT DOCUMENTS

2010/0137775 A1   6/2010  Hu et al.
2014/0276288 A1*  9/2014  Randolph ............ A61H 9/0057
                                                601/152
2020/0069850 A1*  3/2020  Beadle ................. A61M 1/734

* cited by examiner

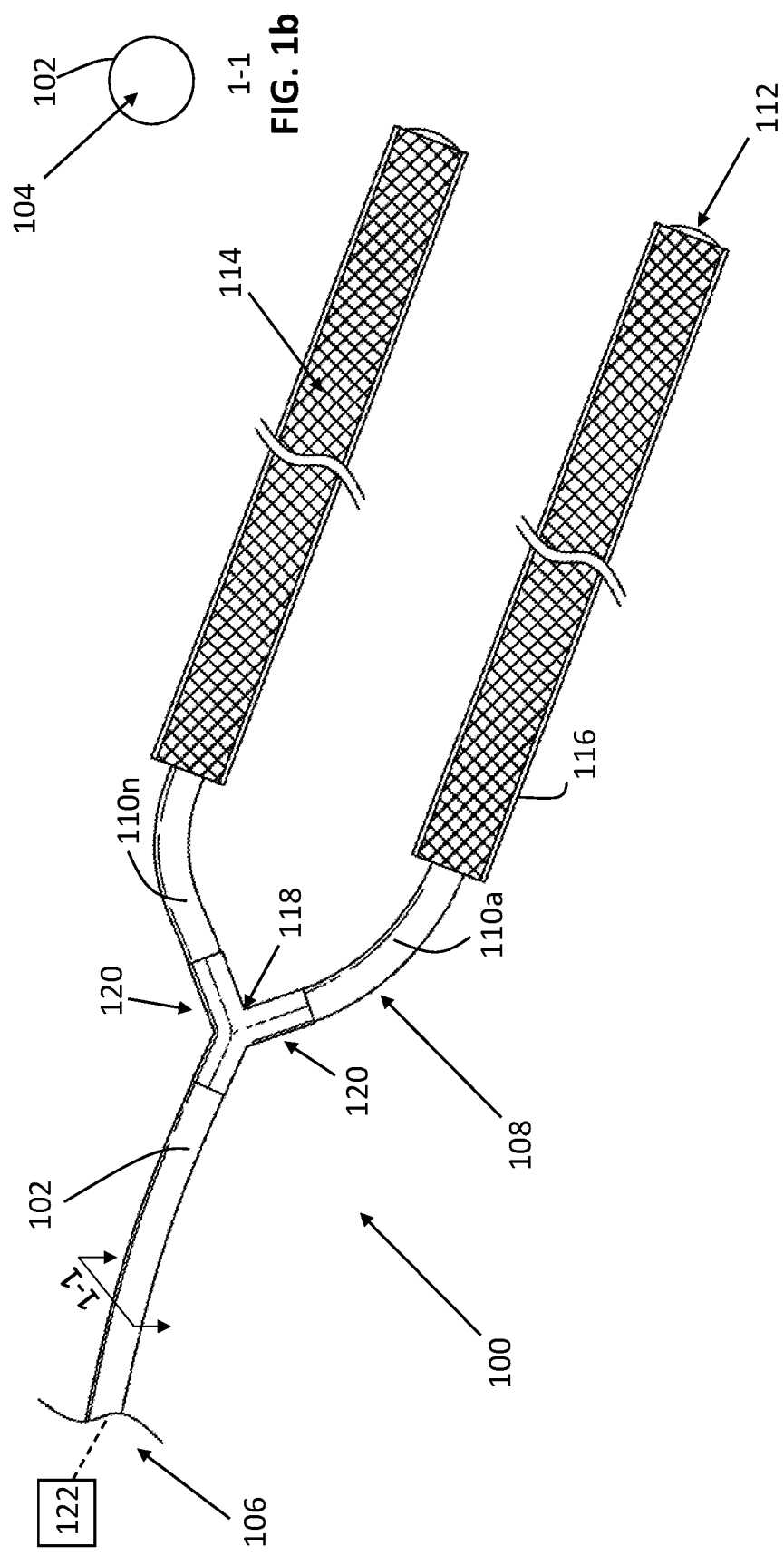

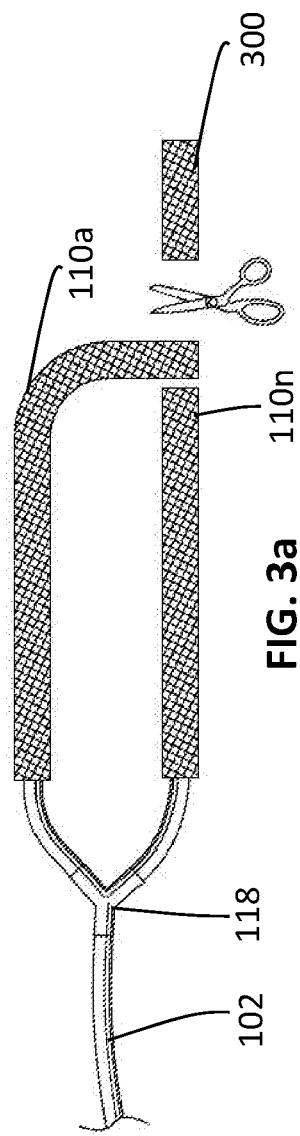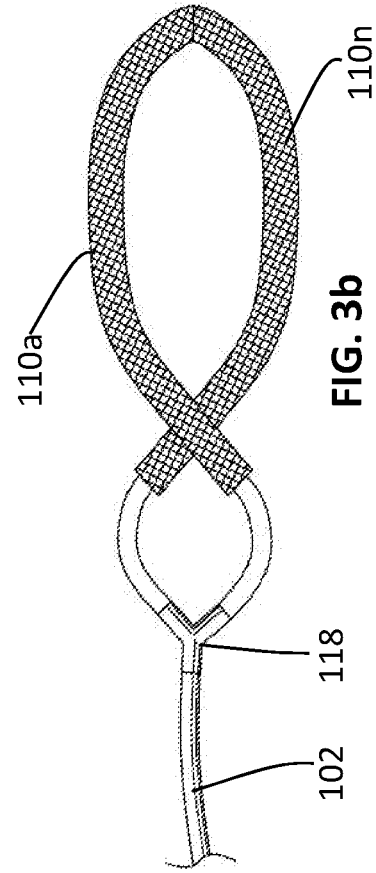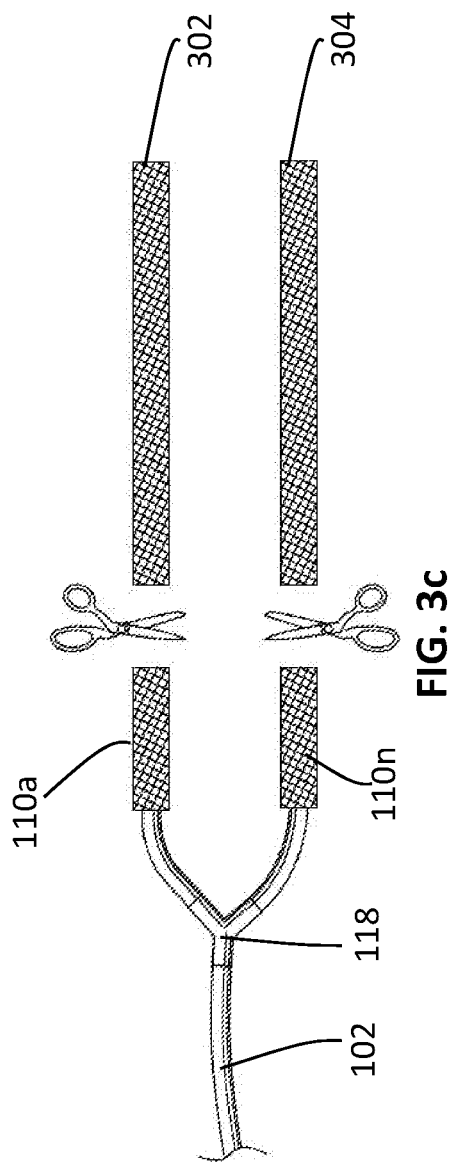

SUCTION-BASED MEDICAL DRESSING AND METHOD OF DERMAL IRRIGATION

FIELD OF THE INVENTION

The present invention relates generally to suction-based medical dressings, and, more particularly, relates to suction-based medical dressings that adheres to the skin at a target area of medical irrigation to a user's dermis.

BACKGROUND OF THE INVENTION

Typically, dermal medical irrigations involve washing of a body cavity or wound by a stream of water or other fluid. A steady, gentle stream is used; and pressure is sufficiently applied to reach the desired area, but not enough to force the fluid beyond the area to be irrigated. Often, pressure is applied manually, such as with a bulb syringe or mechanical device, or by gravity. The greater the height of the container of solution, the greater will be the pressure exerted by the stream of solution. It is known in the art that irrigating units deliver a pulsed flow of fluid. In these devices, a return flow of solution is always allowed for.

Generally, during the irrigation procedure, the medical professional holds an absorbent pad or tissue so that it surrounds the surgical site. Often, the absorbent pad must be held out of the way of the surgical target area, while simultaneously injecting solutions, such as saline, glycine or lactated ringer's solution into the subject area. As each irrigation procedure requires different volumes of fluid delivered at various pressures, and different amounts of fluids, controlling the fluid overflow, and simultaneously focusing on performing the surgical procedure and applying fresh fluid, can be problematic.

Therefore, a need exists to overcome the problems with the prior art as discussed above.

SUMMARY OF THE INVENTION

The invention provides a suction-based medical dressing that overcomes the hereinafore-mentioned disadvantages of the heretofore-known devices and methods of this general type and that includes a vacuum-inducing source operably configured to provide a negative pressure within a tube spanning a length, wherein the length of the tube is surrounded by an absorbent material (e.g., gauze) and having an adhesive thereon. When desired for use, an emergency provider, physician, patient or other user will apply the adhesive side of the occlusive device to an area of a patient where liquid removal is desired and activate the vacuum-inducing source, thereby causing irrigation or other liquid runoff from the patient to be effectively removed for disposal.

With the foregoing and other objects in view, there is provided, in accordance with the invention, a suction-based dressing assembly comprising a flexible tube. The tube defines a tube channel that carries an ambient liquid during dermal irrigation. The tube also defines a proximal tube end forming a proximal tube opening that is fluidly coupled to the tube channel.

The tube also has a bifurcated portion that forms at least two bifurcated tube portions. Each bifurcated tube portion defines a bifurcated tube channel that is fluidly coupled to the tube channel. Each bifurcated tube portion also includes a distal tube end, which is oppositely disposed from the proximal tube end. The bifurcated tube portions also define a plurality of apertures that are fluidly coupled to each respective bifurcated tube channel.

The suction-based dressing assembly provides an absorbent gauze material that surrounds the plurality of apertures on each of the at least two bifurcated tube portions. The absorbent gauze material covers a sufficient area of the bifurcated tube portions, so as to draw the ambient fluid from the patient's skin towards the apertures in the bifurcated tube portions.

The suction-based dressing assembly also provides an occlusive sheet material that at least partially surrounds the absorbent gauze material on at least two sides thereof on each of the bifurcated tube portions. The occlusive sheet material has a bottom surface with an adhesive strip disposed thereon for at least flanking a target irrigation area of a patient's skin.

The suction-based dressing assembly also provides a vacuum assembly that couples to the proximal tube end of the tube channel. The vacuum assembly is operably configured to induce negative pressure within the tube channel and the bifurcated tube channel. The negative pressure in the tube channel causes ambient fluid absorption through a plurality of apertures that form in the tube. Consequently, the ambient liquid being irrigated is drawn out of the saturated absorbent gauze material, and sucked into the tube channel, and the bifurcated tube channel for disposal through a distal tube end In accordance with another feature, an embodiment of the present invention includes the occlusive sheet material at least partially surrounding the absorbent gauze material on three sides thereof. An adhesive strip couples to the bottom surface of the occlusive sheet material. The adhesive strip adheres the occlusive sheet material and the surrounding absorbent gauze material to a target irrigation area of a patient's skin. This adhesive capacity helps retain the assembly in the targeted dermal irrigation area.

In accordance with a further feature of the present invention, the occlusive sheet material is adhesively coupled to the absorbent gauze material on the three sides thereof to form a U-shaped channel that is shaped and sized to receive the absorbent gauze material.

In accordance with a further feature of the present invention, the at least two bifurcated tube portions each further comprise a first end directly coupled together to define a joint. The joint is interposed between the proximal tube end of the flexible tube and the distal tube end of each of the at least two bifurcated tube portions. The at least two bifurcated tube portions each further comprise a bifurcated tube length that separates the joint and the distal tube end. The U-shaped channel of the occlusive sheet material spans at least 50% of the bifurcated tube length. This significant area of coverage by the occlusive sheet material creates a sufficient peripheral boundary to minimize loss of the ambient fluid during dermal irrigation.

In accordance with a further feature of the present invention, an adhesive strip of a polymeric material, couples to the bottom surface of the occlusive sheet material of the at least two bifurcated tube portions, and spans an occlusive sheet material length separating the entire U-shaped channel.

In accordance with a further feature of the present invention, the distal tube end 112 defines a distal tube opening fluidly coupled to the bifurcated tube channel.

In accordance with a further feature of the present invention, the bifurcated portion of the flexible tube is of an oblong shape.

In accordance with a further feature of the present invention, the occlusive sheet further comprises: a bottom wall portion including the bottom surface and an inner surface. The occlusive sheet also includes a sidewall portion directly coupled to the bottom wall portion to form a continuously watertight joint and including an inner surface. The occlusive sheet also includes an upper wall portion directly coupled to the sidewall portion and including an inner surface. The inner surfaces of the bottom wall portion, the sidewall portion, and the upper wall portion surround at least 50% of a circumference defined by the absorbent gauze material spanning at least 50% of the bifurcated tube length.

In accordance with the present invention, a method for dermal irrigation with a suction-based medical dressing includes an initial Step of applying a dermal irrigation procedure to a target irrigation area of the skin.

The method may further comprise a Step of connecting a vacuum assembly to a proximal tube end of a tube, the tube being in fluid communication with at least two bifurcated tube portions having a plurality of apertures.

A Step includes covering a substantial length of the bifurcated tube portions with an absorbent gauze material.

In some embodiments, a Step comprises at least partially surrounding the absorbent gauze material on at least two sides with an occlusive sheet material, the occlusive sheet material having an adhesive strip on a bottom surface.

A Step includes adhering the adhesive strip of the occlusive sheet material to the skin at or near the target irrigation area.

In some embodiments, a Step may include actuating the vacuum assembly to induce negative pressure within the tube and the bifurcated tube.

A Step comprises absorbing, through the absorbent gauze material, ambient fluid residue from the dermal irrigation.

The method may further comprise a Step of sucking the ambient fluid through the apertures in the bifurcated tube, whereby a negative pressure causes the ambient fluid to absorb through the absorbent gauze material, the plurality of apertures, and into the bifurcated tube.

A final Step includes discharging the ambient fluid through a proximal tube opening in the proximal tube end of the tube.

Although the invention is illustrated and described herein as embodied in a suction-based medical dressing and method of dermal irrigation, it is, nevertheless, not intended to be limited to the details shown because various modifications and structural changes may be made therein without departing from the spirit of the invention and within the scope and range of equivalents of the claims. Additionally, well-known elements of exemplary embodiments of the invention will not be described in detail or will be omitted so as not to obscure the relevant details of the invention.

Other features that are considered as characteristic for the invention are set forth in the appended claims. As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one of ordinary skill in the art to variously employ the present invention in virtually any appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward. The figures of the drawings are not drawn to scale.

Before the present invention is disclosed and described, it is to be understood that the terminology used herein is for the purpose of describing particular embodiments only and is not intended to be limiting. The terms "a" or "an," as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically. The term "providing" is defined herein in its broadest sense, e.g., bringing/coming into physical existence, making available, and/or supplying to someone or something, in whole or in multiple parts at once or over a period of time. Also, for purposes of description herein, the terms "upper", "lower", "left," "rear," "right," "front," "vertical," "horizontal," and derivatives thereof relate to the invention as oriented in the figures and is not to be construed as limiting any feature to be a particular orientation, as said orientation may be changed based on the patient's perspective of the device. Furthermore, there is no intention to be bound by any expressed or implied theory presented in the preceding technical field, background, brief summary or the following detailed description.

As used herein, the terms "about" or "approximately" apply to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure. In this document, the term "longitudinal" should be understood to mean in a direction corresponding to an elongated direction of the tubes.

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and explain various principles and advantages all in accordance with the present invention.

FIG. 1a is a top view of a suction-based medical dressing assembly, in accordance with the present invention;

FIG. 1b is a sectioned side view of an exemplary flexible tube, according to section plane 1-1 in FIG. 1a, showing the tube channel, in accordance with the present invention;

FIG. 3a is a top view of the distal tube ends of the bifurcated tube portions bending, and a terminal section of the distal tube ends being cut, in accordance with the present invention;

FIG. 3b is a top view of the bifurcated tube length of the bifurcated tube portions being twisted, and joined at the distal tube, in accordance with the present invention;

FIG. 3c is a top view of two significant portions of the bifurcated tube portions being cut to form two significantly shorter bifurcated tube portions, in accordance with the present invention;

DETAILED DESCRIPTION

Figures 2A, 2B:
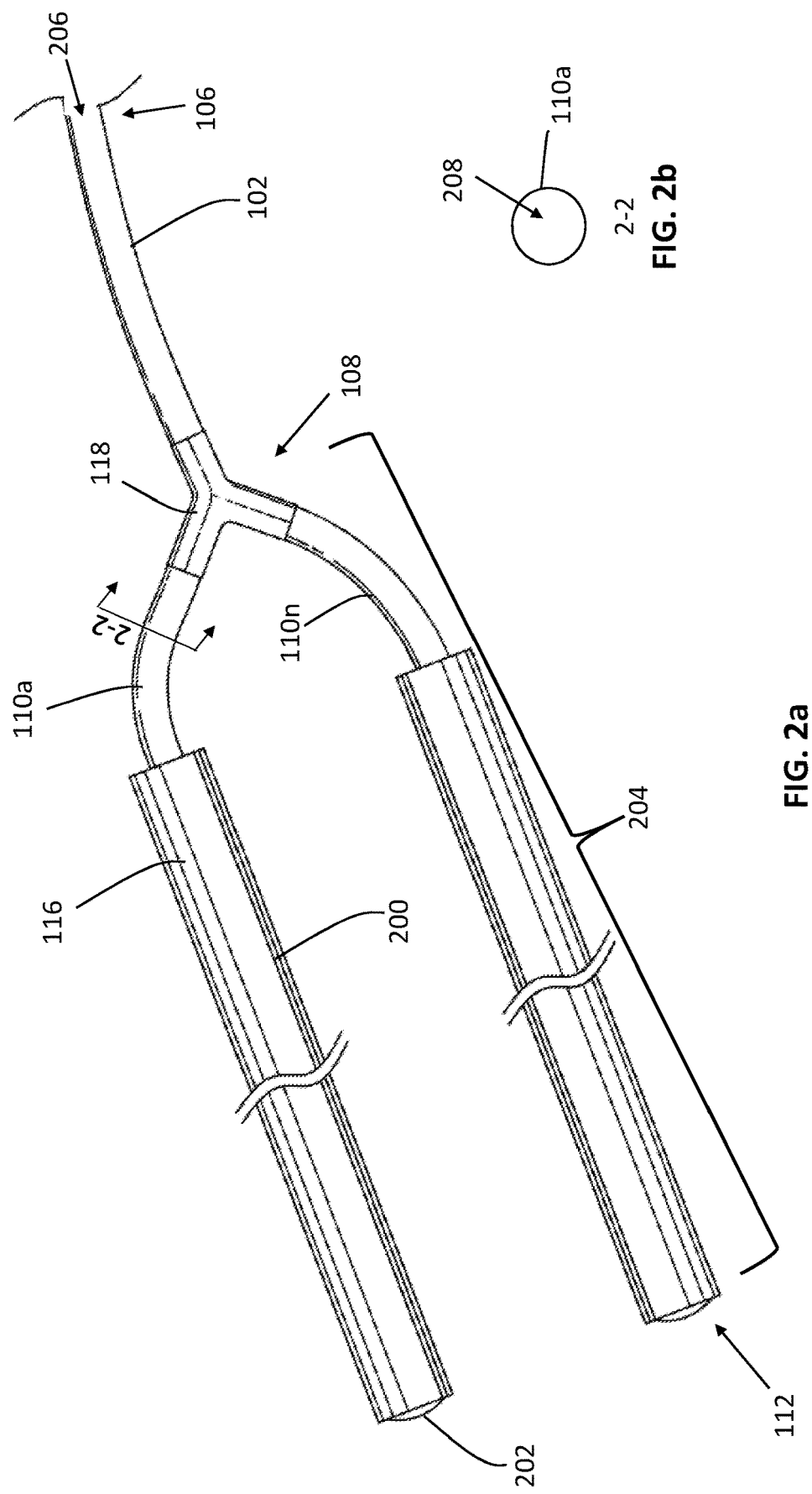
FIG. 2a is a bottom view of the suction-based medical dressing assembly shown in FIG. 1a, in accordance with the present invention.
FIG. 2b is a sectioned side view of an exemplary bifurcated tube portion, according to section plane 2-2 in FIG. 2a, showing the tube channel, in accordance with the present invention.

While the specification concludes with claims defining the features of the invention that are regarded as novel, it is believed that the invention will be better understood from a consideration of the following description in conjunction with the drawing figures, in which like reference numerals are carried forward. It is to be understood that the disclosed embodiments are merely exemplary of the invention, which can be embodied in various forms.

Referring now to FIG. 1a, one embodiment of the present invention is shown in a perspective view. FIG. 1a, along with the other figures depicted herein, shows several advantageous features of the present invention, but, as will be described below, the invention can be provided in several shapes, sizes, combinations of features and components, and varying numbers and functions of the components.

The present invention provides a novel and efficient suction-based medical dressing assembly 100 and method 1400 of dermal irrigation. Embodiments of the invention provide a vacuum-inducing source operably configured to provide a negative pressure within a tube 102 spanning a length, wherein the length of the tube is surrounded by an absorbent material 114 (e.g., gauze) covered substantially with an occlusive sheet material 116, and having an adhesive strip 200 thereon for placement on a user. When desired for use, a patient or other user (e.g., an emergency responder) will apply the adhesive side of the occlusive device to an area of a patient where liquid removal is desired and activate the vacuum-inducing source, thereby causing irrigation or other fluid runoff from the patient to be effectively and efficiently removed for disposal.

Those skilled in the art will recognize that performing a surgical procedure while simultaneously applying the fluid to the subject area can result in fluid spilling onto and over a patient, the medical professional, and the floor. This can be problematic when the fluid is bio-hazardous material or otherwise has medical-related issues. The present invention works to both absorb and intake the ambient fluid from across the patient's skin 400, to minimize excess fluid spillage.

Figure 4:
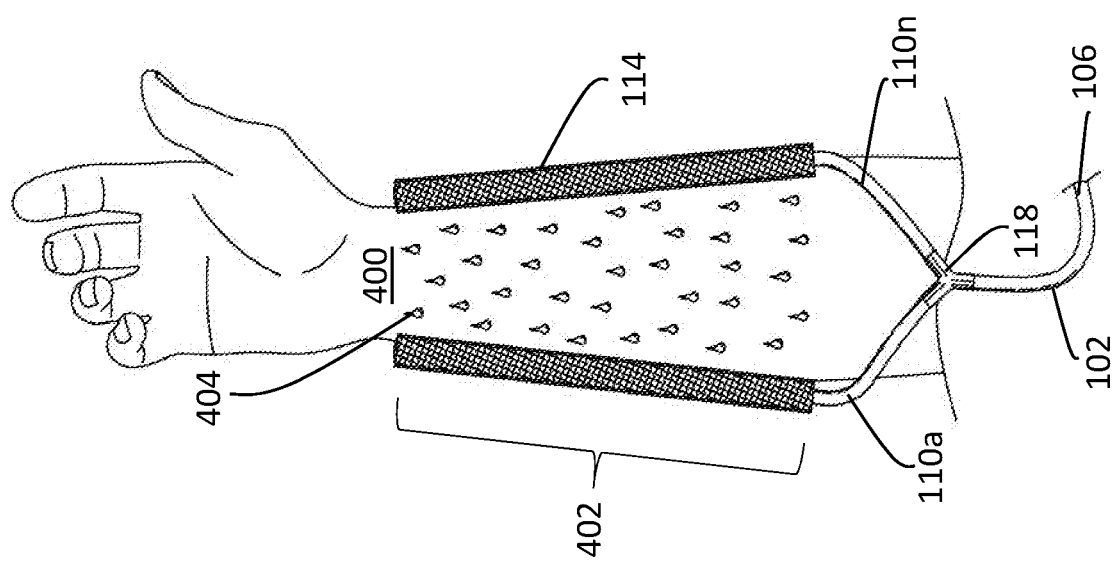
FIG. 4 is a perspective view of the suction-based medical dressing assembly shown in FIG. 1a adhering to an arm during dermal irrigation, in accordance with the present invention.

With reference to FIG. 1a and FIG. 4, the first example of the suction-based medical dressing assembly 100, hereafter "assembly 100" is shown. The assembly 100 provides a flexible tube 102 that is configured to carry and discharge an ambient fluid 404 from the patient's skin 400 during a dermal irrigation procedure. The fluid 404 may include, without limitation, water, saline, glycine, and lactated ringer's solution. The tube 102 defines a tube channel 104 that is sized and dimensioned to carry the ambient fluid 404 in a smooth-flowing rate during the dermal irrigation procedure. The tube 102 also defines a proximal tube end 106 forming a proximal tube opening 206 that is fluidly coupled to the tube channel 104 (FIG. 1b). Suitable materials for the tube 102 may include, without limitation, medical grade silicone and medical grade polyvinyl chloride (PVC), and latex rubber.

Turning now to FIG. 2a, the bottom view of the assembly 100 shows that the tube 102 may include a section that is linear, and a section that forms a bifurcated portion 108. The bifurcated portion 108 separates to form at least two bifurcated tube portions 110a-n (wherein "n" represents any number greater than two). In one embodiment, the bifurcated portion 108 of the flexible tube is of an oblong shape, or elongated and rectangular or ovular in shape. However, in yet other embodiments, the bifurcated tube portions 110a-n are shaped and sized substantially the same as the tube, forming a unitary conduit therewith.

The bifurcated tube portions 110a-n comprises a first end 120 directly coupled together to define a joint 118. As FIG. 2b shows, the joint 118 is interposed between the proximal tube end 106 of the flexible tube and the distal tube end 112 of each of the bifurcated tube portions 110a-n. The distal tube end 112 defines a distal tube opening 202 fluidly coupled to the bifurcated tube channel 208 through the joint 118. The joint 118 has smooth surfaces and branches each bifurcated tube portions 110a-n outwardly between 30° to 90°. This angle of bifurcation allows each bifurcated tube portion to cover multiple body parts, i.e., two arms, two legs, during the dermal irrigation.

The integral configuration of the joint 118 between the tube 102 and the bifurcated tube portions 110a-n creates a smooth flow of ambient fluid 404 between the bifurcated portion 108 and the linear portion of the tube 102. Further, each bifurcated tube portion 110a-n defines a bifurcated tube channel 208 that is fluidly coupled to the tube channel 104 (FIG. 2b). The bifurcated tube channel 208 is defined by about the same diameter, surface area, and material composition of the tube channel 104.

As FIG. 1a shows, the bifurcated tube portions 110a-n comprise a bifurcated tube length 204 that separates the joint 118 and the distal tube end 112. Each bifurcated tube portion 110a-n also includes a distal tube end 112, which is oppositely disposed from the proximal tube end. The distance from the distal tube end 112 to the proximal tube end 106 can be beneficially varied by bending, twisting, and cutting a section of the bifurcated tube length 204 or the distal tube ends 112.

For example, FIG. 3a shows the distal tube ends 112 of the bifurcated tube portions 110a-n bending to join in fluid communication, and a terminal section 300 of the distal tube ends 112 being cut off to shorten one of the bifurcated tube portions 110a-n. FIG. 3b shows the bifurcated tube length 204 of the bifurcated tube portions 110a-n being twisted, and joined at the distal tube ends 112. Continuing further, FIG. 3c shows two significant portions 302, 304 of the bifurcated tube portions 110a-n being cut to form two significantly shorter bifurcated tube portions 110a-n. It is also significant to note that bifurcated tube portions 110a-n can be extended by joining sections of tubing through medical tubing couplers known in the art.

And, as FIG. 4 shows, the length of the tube 102 and bifurcated tube portions 110a-n is dependent on the region of the patient's body that requires the dermal irrigation. For example, if the fluid is dripping longitudinally along the arm of the patient, the tube 102 and the bifurcated tube portions 110a-n may each be approximately 1-2' feet long, to provide sufficient length for dermal irrigation along the arms. However, if the assembly 100 is applied to the head or eyes, shorter bifurcated tube portions 110a-n are required; and may be cut to accommodate this length requirement (FIG. 3c).

Figure 5:
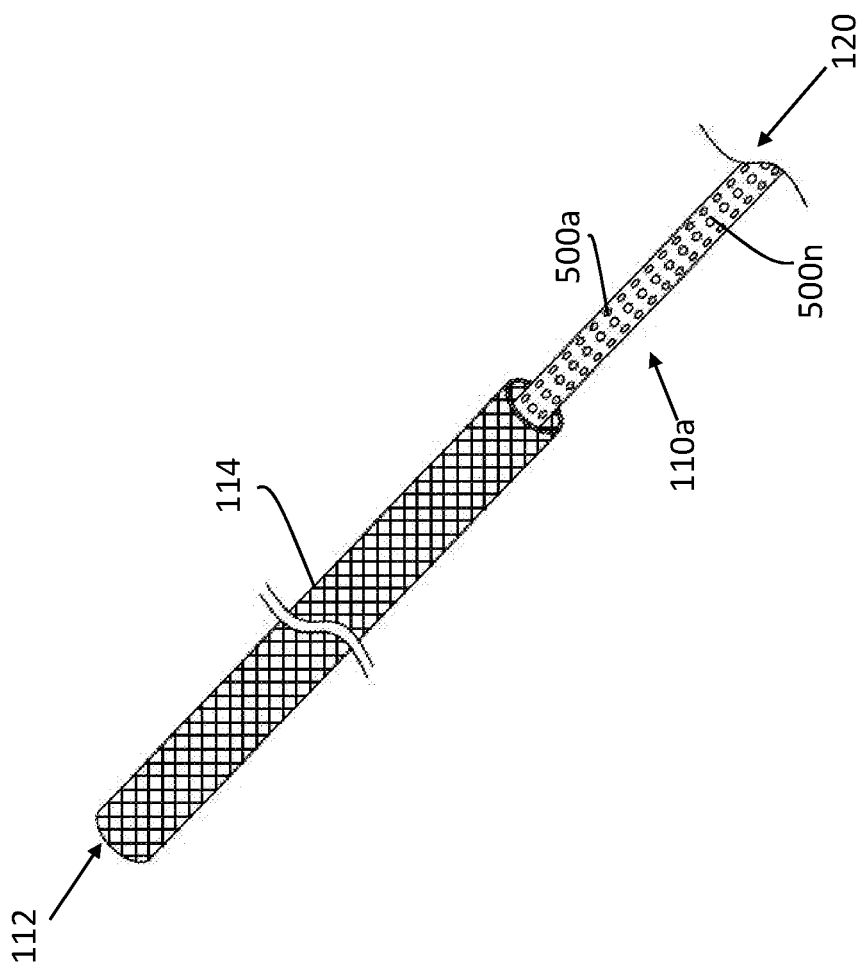
FIG. 5 is a perspective view of an exemplary absorbent gauze material partially covering the bifurcated tube portion, in accordance with the present invention.

As shown in FIG. 5, which depicts a partially sectioned and fragmentary view, the bifurcated tube portions 110a-n also define a plurality of apertures 500a-n that are fluidly coupled to each respective bifurcated tube channel 208. The apertures 500a-n serve to enable passage of the ambient fluid 404 into the bifurcated tube channel 208, and subsequently, the tube channel 104 for discharge. The apertures 500a-n may form circular shapes and be disposed in an equal-spaced apart relationship along the entire or partial length(s) of the bifurcated tube length 204. However, since the purpose of the apertures 500a-n is to intake the ambient fluid, the apertures 500a-n may be depressed into the surface of the bifurcated tubes, such that the fluid more easily flows into the bifurcated tube channel 208.

Turning again to FIG. 5, the assembly 100 provides an absorbent gauze material 114 that surrounds the bifurcated tube portions 110a-n, substantially covering the apertures 500a-n in the process. The absorbent gauze material 114 covers a sufficient area and length of the bifurcated tube portions 110a-n, so as to draw the ambient fluid from the patient's skin 400 towards the apertures 500a-n in the bifurcated tube portion. In one alternative use, the absorbent gauze material 114 can be manually squeezed periodically to enhance the absorption of fluid 404 during the dermal irrigation process. In this manner, the fluid 404 is absorbed into the apertures 500a-n of the bifurcated tube portions 110a-n, while also being squeezed out of the absorbent gauze material 114.

In one non-limiting embodiment, the absorbent gauze material 114 is a porous material acceptable for medical use. However, in other embodiments, the absorbent gauze material 114 is a light, open-meshed fabric of muslin or similar material used in bandages, dressings, and surgical sponges. In yet other embodiments, the absorbent gauze material 114 may be white cotton cloth of various thread counts and weights, supplied in various lengths and widths and in different forms, i.e., rolls, folds.

Figure 6:
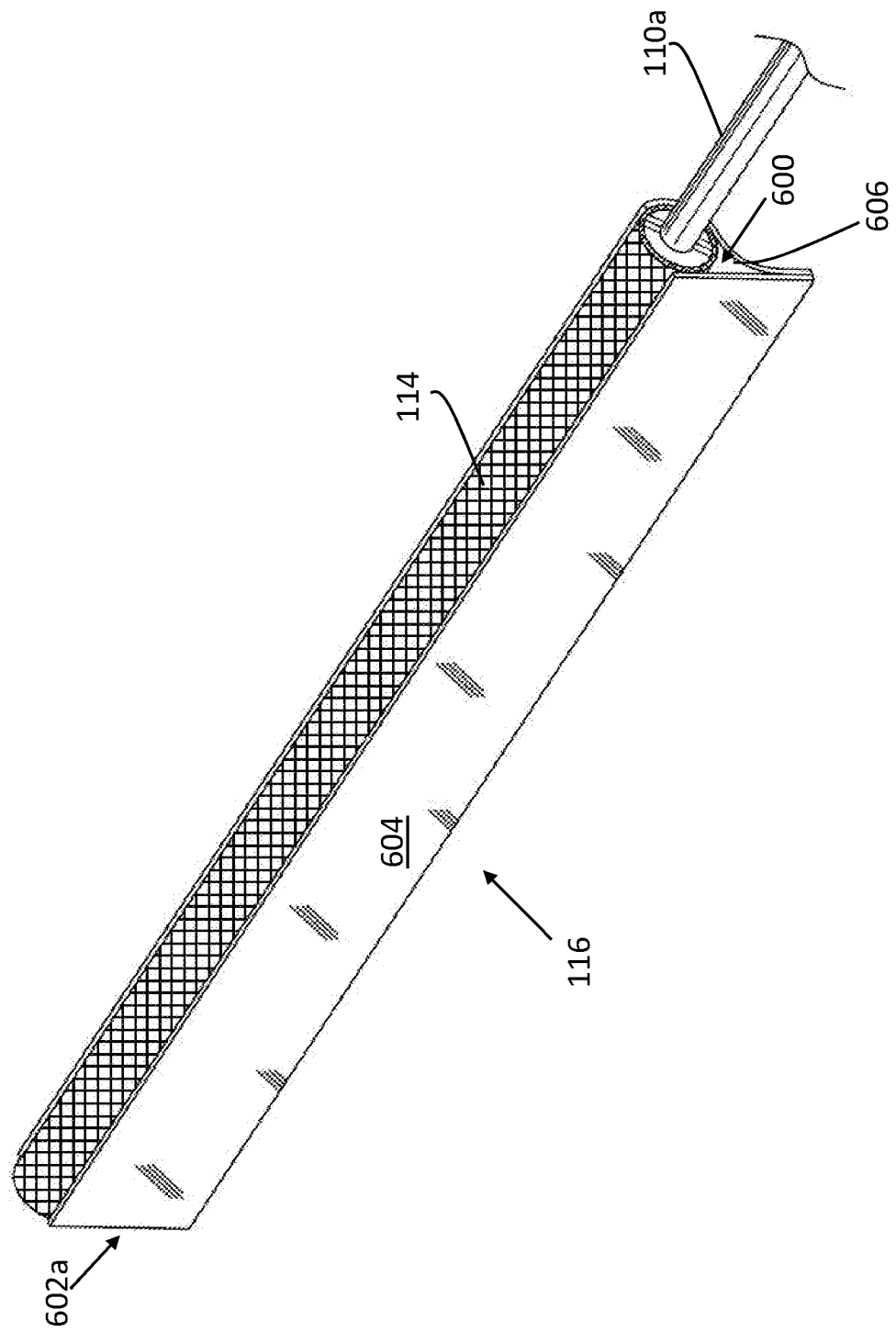
FIG. 6 is a perspective view of an exemplary occlusive sheet material partially covering the absorbent gauze material, in accordance with the present invention.

As FIG. 6 illustrates, the assembly 100 also provides an occlusive sheet material 116 that is detachably attachable, or integral, to each of the bifurcated tube portions 110a-n. The occlusive sheet material 116 may be an impermeable, resilient, thin polymeric layer that works to segregate the fluid between the patient's skin 400 and the absorbent gauze material 114. The occlusive sheet material 116 comprises a bottom wall portion 602a, 602b that engages the absorbent gauze material 114. The bottom wall portion 602a-b is defined by a bottom surface 604 and an inner surface 606. A sidewall portion 704a, 704b directly couples to the bottom wall portion 602a-b. The sidewall portion 704a-b includes an inner surface 706 that forms a continuously watertight joint with the absorbent gauze material 114 (FIG. 10a).

Figure 10:
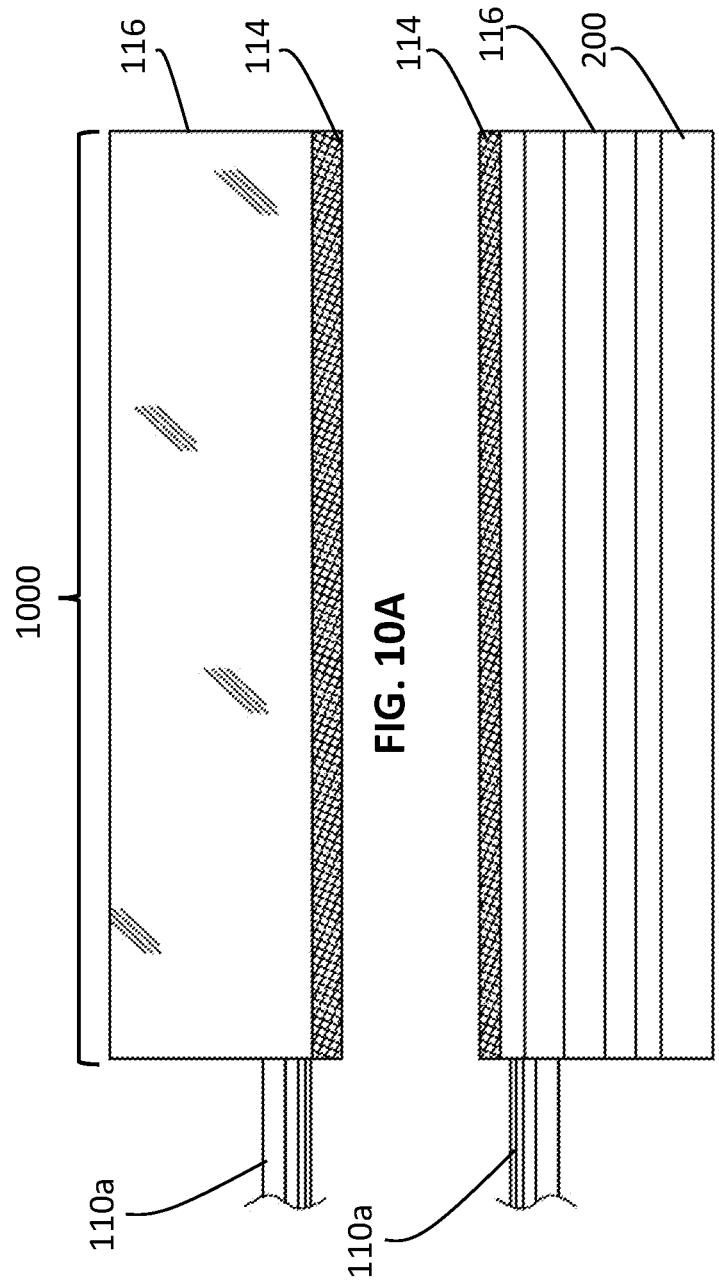
FIG. 10a is a left-side view of the occlusive sheet material covering the bifurcated tube portion, in accordance with the present invention.
FIG. 10b is a right-side view of the occlusive sheet material covering the bifurcated tube portion, in accordance with the present invention.

Continuing with the construction of the occlusive sheet material 116, the occlusive sheet material 116 also includes an upper wall portion 700a, 700b directly coupled to the sidewall portion 704a-b and including an inner surface 702 (FIG. 10b). In one non-limiting embodiment, the inner surfaces 606, 706, 702 of the bottom wall portion 602a-b, the sidewall portion 704a-b, and the upper wall portion 700a-b surround at least 50% of a circumference defined by the absorbent gauze material 114, and span at least 50% of the bifurcated tube length 204.

The walls 602a-b, 700a-b, 704a-b of the occlusive sheet material 116 completely resist the transfer of fluid 404 through the occlusive sheet material 116. In some embodiments, the occlusive sheet material may be at least 90% resistant to fluid penetration. However, in alternative embodiments, the occlusive sheet material 116 is partially porous and partially impermeable. This gradient porosity allows the flow of the fluid 404 to be regulated towards a specific section of the absorbent gauze material 114. Thus, the occlusive sheet material 116 can be effective for regulating flowage of the fluid towards the absorbent gauze material 114. In another useful function, the occlusive sheet material 116 also enables fixed connectivity to the irrigation target area 402 on the skin 400 through use of an adhesive strip 200.

Figure 7:
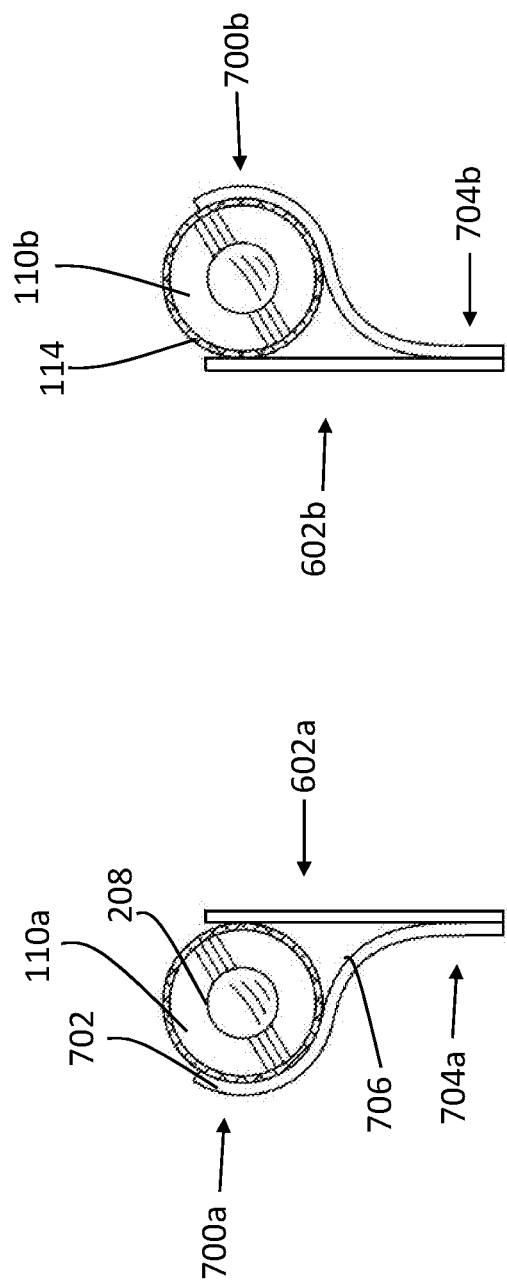
FIG. 7a is a sectioned side view of an exemplary occlusive sheet material partially covering the absorbent gauze material and a first bifurcated tube portion, in accordance with the present invention.
FIG. 7b is a sectioned side view of an exemplary occlusive sheet material partially covering the absorbent gauze material and a second bifurcated tube portion, in accordance with the present invention.

Looking again at FIG. 6, the occlusive sheet material 116 is configured to at least partially surround the absorbent gauze material 114 on at least two sides thereof, creating a partial encapsulation. However, in other embodiments, the occlusive sheet material 116 more fully encapsulates the absorbent gauze material 114 by surround three sides of the absorbent gauze material 114 (FIGS. 7A-7B). In this three-sided configuration, the occlusive sheet material 116 forms a U-shaped channel 600 that is shaped and sized to receive the absorbent gauze material 114.

Figure 8:
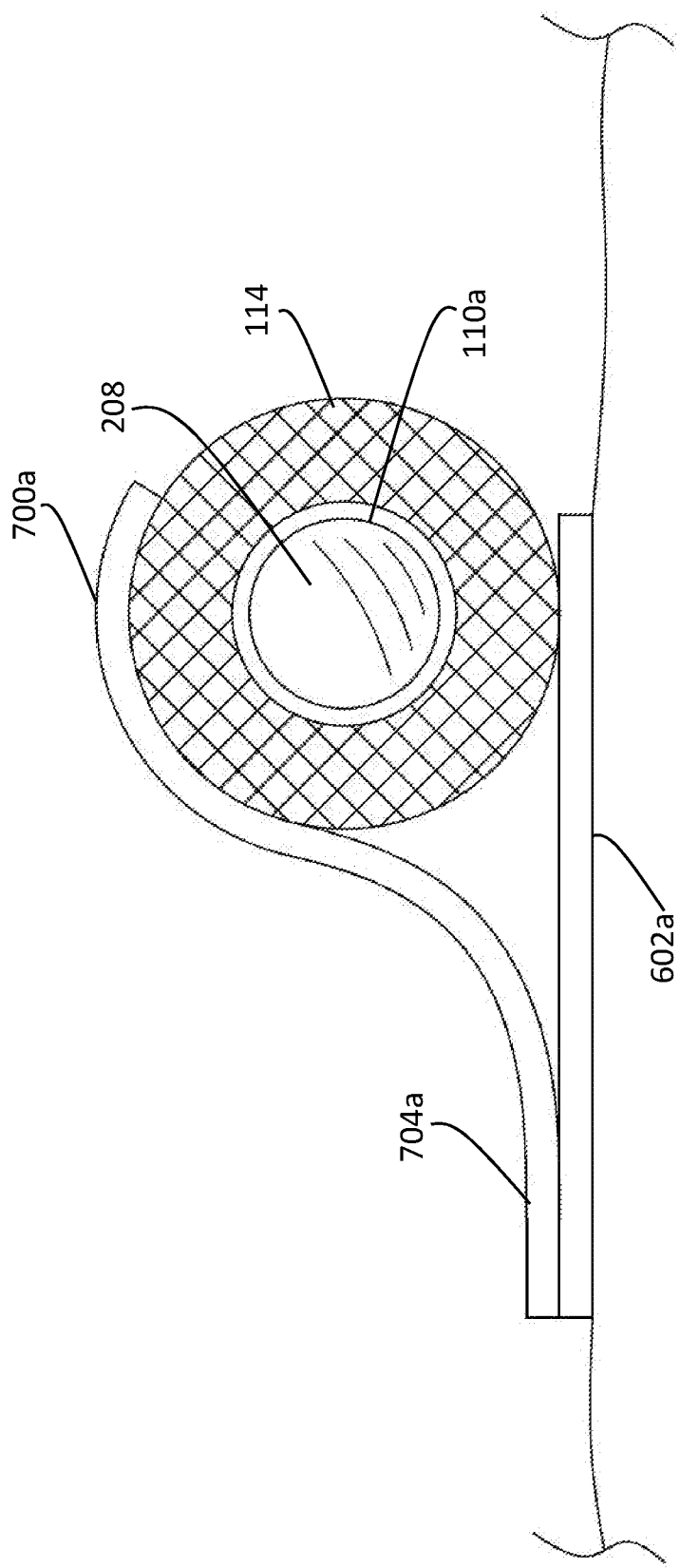
FIG. 8 is a sectioned side view of the sidewall, bottom wall, and upper wall of the occlusive sheet material covering the absorbent gauze material, in accordance with the present invention.
Figure 9:
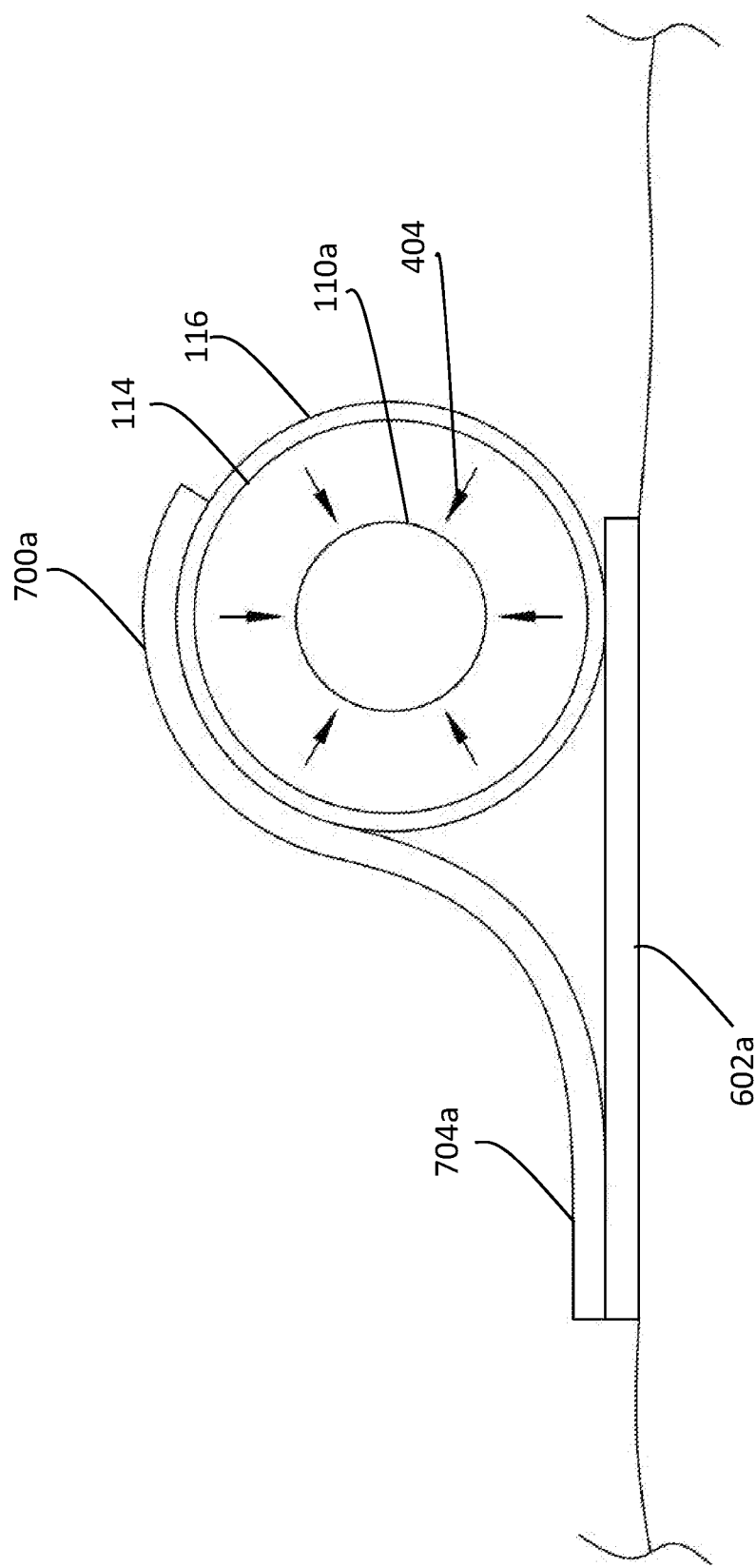
FIG. 9 is a sectioned side view of the sidewall, bottom wall, and upper wall of the occlusive sheet material covering the absorbent gauze material, showing the ambient fluid being drawn into the bifurcated tube channel, in accordance with the present invention.

In another unique configuration provided by the occlusive sheet material 116, the U-shaped channel 600 forms from the walls 602a-b, 700a-b, 704a-b, between the occlusive sheet material 116 and the absorbent gauge 114. This is illustrated in the sectioned view of FIG. 8. The U-shaped channel 600 formed by the occlusive sheet material 116 spans at least 50% of the bifurcated tube length 204. However, in other embodiments, the U-shaped channel 600 spans approximately 80% to 90% of the bifurcated tube length 204, so as to provide a sufficient boundary for irrigation of the fluid 404. As FIG. 9 shows, this significant area of coverage by the occlusive sheet material 116 around the absorbent gauge 114 creates a sufficient peripheral boundary to minimize loss of the ambient fluid 404 during dermal irrigation.

In some embodiments, an adhesive strip 200 couples to the bottom surface 604 at the bottom wall portion 602*a-b* of the occlusive sheet material 116. The adhesive strip 200 is configured to adhere the occlusive sheet material 116 and the surrounding absorbent gauze material 114 to a target irrigation area 402 of a patient's skin 400. In one embodiment, the adhesive strip 200 spans an occlusive sheet material length 1000, separating the entire U-shaped channel 600 (FIG. 10*a*). Through this connective arrangement, the adhesive strip 200 is used for at least flanking the absorbent gauze material 114 against a target irrigation area 402 of a patient's skin 400.

In this manner, the adhesive capacity provided by the assembly 100 helps retain the absorbent gauze material 114 (and bifurcated tube portions 110*a-n* contained therein) in the targeted dermal irrigation area. In one non-limiting embodiment, the adhesive strip 200 is fabricated from a polymeric material. Though in other embodiments, a paste adhesive, or a sticky polymer, or a hook and loop fastener may be used for adherence.

In some embodiments, the assembly 100 also provides a vacuum assembly 122 that operatively couples to the proximal tube end 106 of the tube channel 104 (FIG. 1). The vacuum assembly 122 is configured to induce negative pressure inside the tube channel 104 and the bifurcated tube channel 208, creating a vacuum through the length of the tubes 102, 110*a-n*. In one non-limiting embodiment, the vacuum assembly 122 is a vacuum pump. The vacuum assembly 122 may induce sufficient negative pressure to draw ambient fluid through the tube and the bifurcated tube portions 110*a-n*.

The negative pressure in the tube channel 104 creates fluid absorption through the apertures 500*a-n* in the bifurcated tube portion. Consequently, the ambient liquid being irrigated from the patient's skin 400 is drawn out of the saturated absorbent gauze material 114 and sucked into the bifurcated tube channel 208 for disposal through the proximal tube opening 206 in the proximal tube end 106 of the tube. In one non-limiting embodiment, the pressure is approximately 5-12 PSIA. Those skilled in the art will recognize that gauze pressure is measured relative to ambient atmospheric pressure, which is approximately 14.7 PSIA. Said differently and looking at FIG. 1, FIG. 4, and FIGS. 7*a-b*, the at least two bifurcated tube portions 110*a-n* each span outwardly from the joint 118 and define an open space between outer surfaces of the absorbent porous material 114 surrounding each of the at least two bifurcated tube portions 110*a-n* for flanking the target irrigation area 402 on the user's skin 400, wherein the open space is disposed for receiving ambient liquid 404 over the target irrigation area 402 thereby causing, with the induced negative pressure within the tube channel 104 and the bifurcated tube channel 208 by the vacuum assembly 122, ambient fluid absorption through the plurality of apertures 500*a-n* and into the tube channel 104 and the bifurcated tube channel 208.

Figure 11:
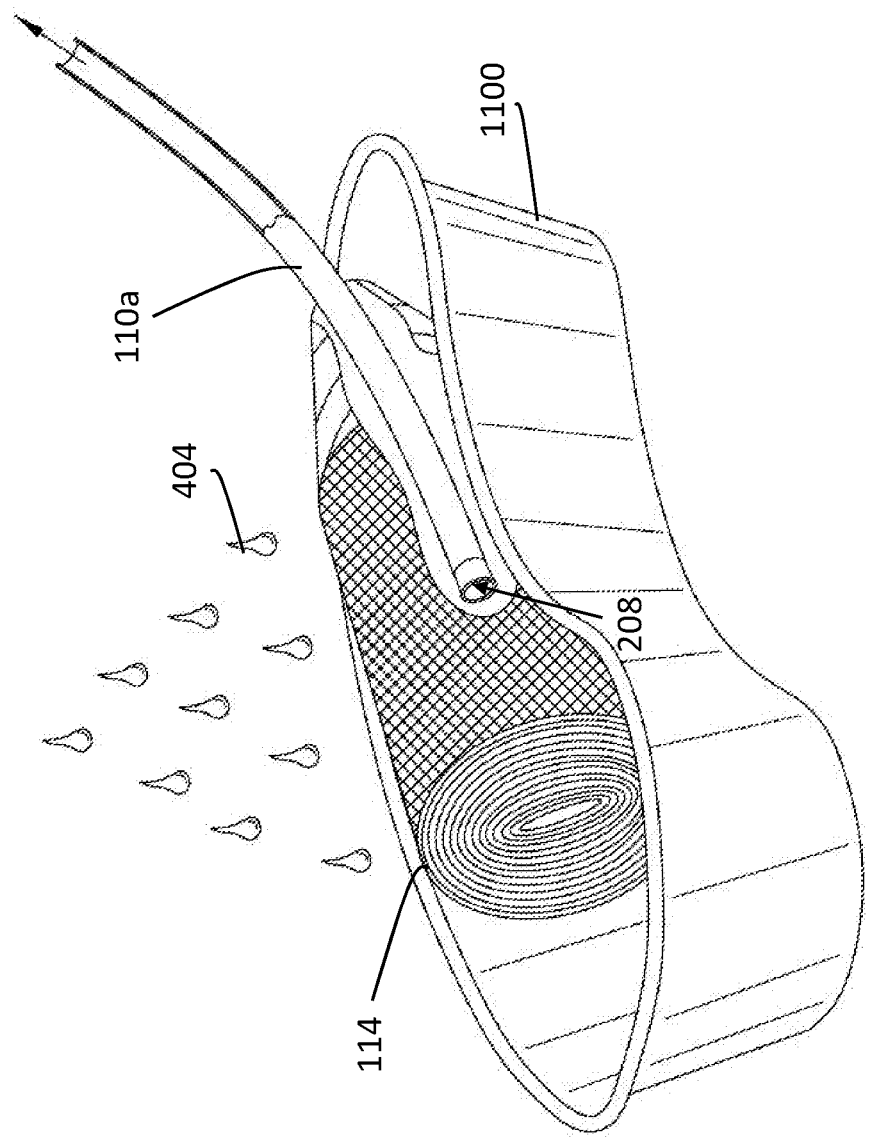
FIG. 11 is a perspective view of the suction-based medical dressing assembly retained in a basin, in accordance with the present invention.

As discussed above, the assembly 100 is operable in a target irrigation area where dermal irrigation occurs. The irrigation utilizes a fluid 404, such as a saline liquid, to wash, clean, and flush a wound or area of the skin. Despite the fluid 404 being drawn into the absorbent gauze material 114, and the apertures 500*a-n* through the bifurcated tube channel 208, the fluid 404 can still overflow. This is often the case when the medical procedure requires large quantities of fluid. In this irrigation scenario, FIG. 11 illustrates how a basin 1100 can be used to carry the absorbent gauze material 114 and bifurcated tube portions 110*a-n*. Thus, the possible hazardous fluid does not spill on the patient or ground, but continues to be absorbed into the assembly 100 and retained in the basin 1100.

Figure 12:
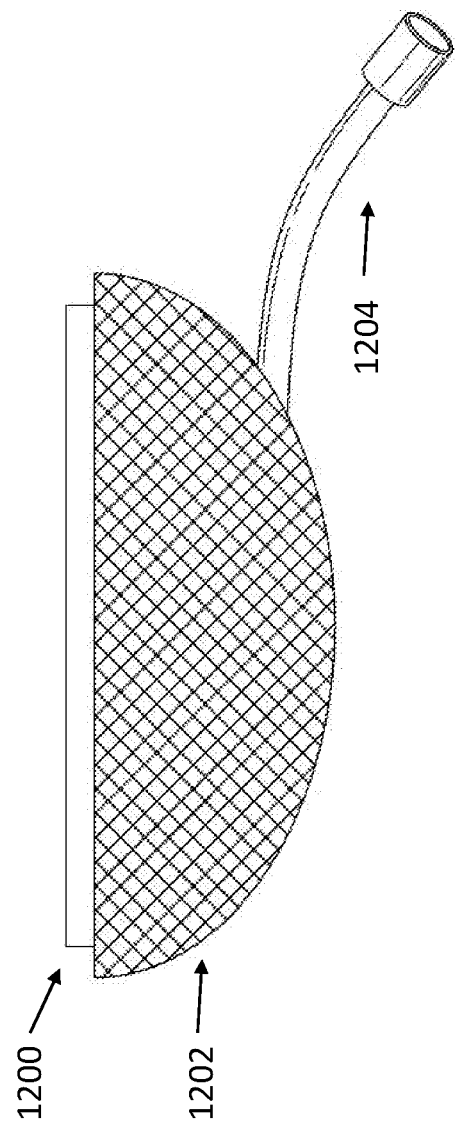
FIG. 12 is a sectioned side view of an exemplary ovulated-shaped bifurcated tube portion covered in an absorbent gauze material, in accordance with the present invention.
Figure 13:
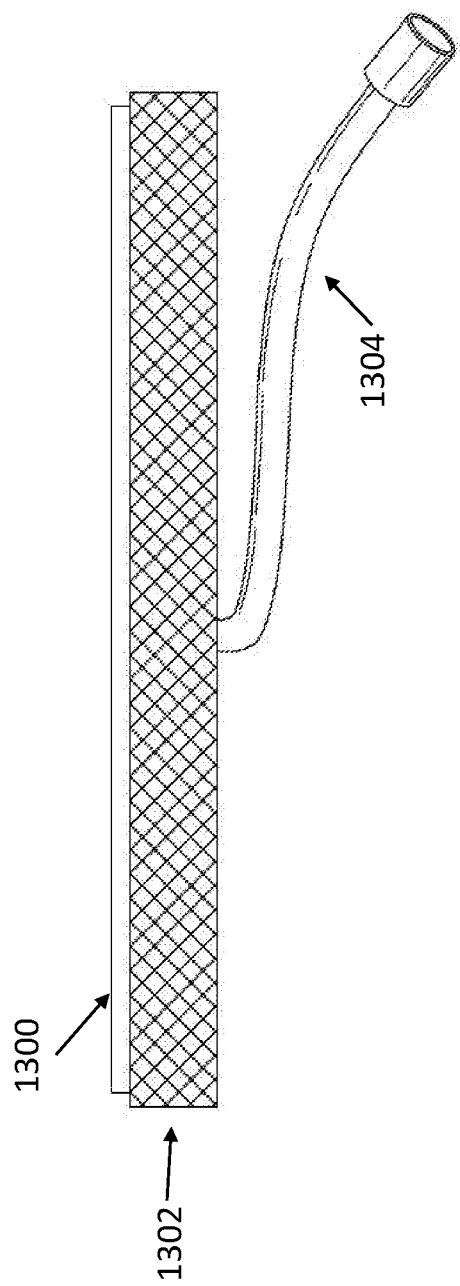
FIG. 13 is a sectioned side view of an exemplary rectangular-shaped bifurcated tube portion covered in an absorbent gauze material, in accordance with the present invention.

In other unique dermal irrigation scenarios, FIG. 12 shows an oblong, or ovular-shaped bifurcated tube channel 1200 used to carry the fluid 404. In this configuration, an absorbent gauze material 1202 encapsulates the ovular-shaped bifurcated tube channel 1200, taking substantially the same shape. And as discussed above, a flexible tube 1204 carries the fluid for discharge under influence of the negative pressure in the tube channel. In yet another configuration, FIG. 13 shows a rectangular shaped bifurcated tube channel 1300 used to carry the fluid 404. In this configuration, an absorbent gauze material 1302 encapsulates the rectangular shaped bifurcated tube channel 1300. A medical grade, flexible tube in fluid communication with the rectangular shaped bifurcated tube channel 1300 receives the fluid 404 for discharge thereof.

Figure 14:
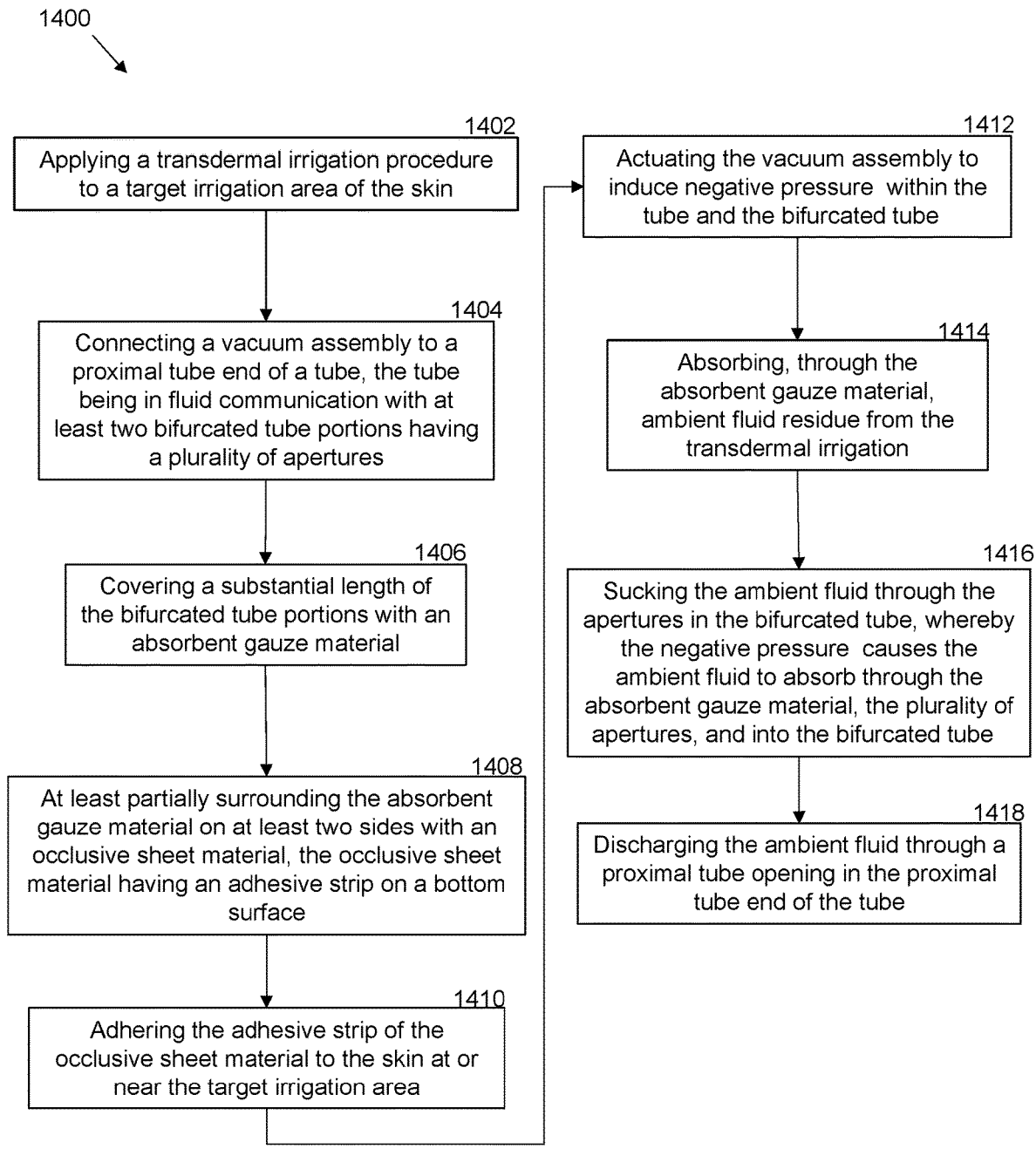
FIG. 14 is a flowchart of an exemplary method of dermal irrigation with suction-based dressing assembly, in accordance with the present invention.

FIG. 14 will be described in conjunction with the process flow chart. Although FIG. 14 shows a specific order of executing the process steps, the order of executing the steps may be changed relative to the order shown in certain embodiments. Also, two or more blocks shown in succession may be executed concurrently or with partial concurrence in some embodiments. Certain steps may also be omitted in FIG. 14 for the sake of brevity. In some embodiments, some or all of the process steps included in FIG. 14 can be combined into a single process.

As the flowchart illustrates, a method 1400 for dermal irrigation with a suction-based medical dressing includes an initial Step 1402 of applying a dermal irrigation procedure to a target irrigation area of the skin. This can include an area where fluid runoff from medical irrigation is occurring. The method 1400 may further comprise a Step 1404 of connecting a vacuum assembly to a proximal tube end of a tube, the tube being in fluid communication with at least two bifurcated tube portions having a plurality of apertures. The vacuum assembly creates a negative pressure in the tube and the bifurcated tube portions.

A Step 1406 includes covering a substantial length of the bifurcated tube portions with an absorbent gauze material. The absorbent gauze material works to absorb the fluid directly from the skin. In some embodiments, a Step 1408 comprises at least partially surrounding the absorbent gauze material on at least two sides with an occlusive sheet material, the occlusive sheet material having an adhesive strip on a bottom surface. The occlusive sheet material serves as a watertight joint to prevent the fluid from seeping through the tubes and absorbent gauze. A Step 1410 includes adhering the adhesive strip of the occlusive sheet material to the skin at or near the target irrigation area. This affixes the absorbent gauge and tubes in the desired irrigation target area.

In some embodiments, a Step 1412 may include actuating the vacuum assembly to induce negative pressure within the tube and the bifurcated tube. A low pressure is created in the tubes. A Step 1414 comprises absorbing, through the absorbent gauze material, ambient fluid residue from the dermal irrigation. The method 1400 may further comprise a Step 1416 of sucking the ambient fluid through the apertures in the bifurcated tube, whereby the negative pressure causes the ambient fluid to absorb through the absorbent gauze material, the plurality of apertures, and into the bifurcated tube A final Step 1418 includes discharging the ambient fluid through a proximal tube opening in the proximal tube end of the tube. This discharge of fluid continues until the medical irrigation is complete.

Although the process-flow diagrams show a specific order of executing the process steps, the order of executing the steps may be changed relative to the order shown in certain embodiments. Also, two or more blocks shown in succession may be executed concurrently or with partial concurrence in some embodiments. Certain steps may also be omitted from the process-flow diagrams for the sake of brevity. In some embodiments, some or all the process steps shown in the process-flow diagrams can be combined into a single process.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the above described features.

What is claimed is:

1. A suction-based dressing assembly comprising:
   a flexible tube:
      defining a tube channel and having a proximal tube end defining a proximal tube opening fluidly coupled to the tube channel; and
      having a bifurcated portion with at least two bifurcated tube portions each spanning outwardly from a joint and each defining a bifurcated tube channel fluidly coupled to the tube channel and each of the at least two bifurcated tube portions including a distal tube end, the at least two bifurcated tube portions defining a plurality of apertures thereon fluidly coupled to each respective bifurcated tube channel;
   an absorbent porous material surrounding the plurality of apertures on one of the at least two bifurcated tube portions and an absorbent porous material surrounding the plurality of apertures on another of the at least two bifurcated tube portions;
   an occlusive sheet material disposed on the one of the at least two bifurcated tube portions, at least partially surrounding the absorbent porous material on at least two sides thereof, and having a bottom surface with an adhesive strip disposed thereon;
   an occlusive sheet material disposed on the another of the at least two bifurcated tube portions, at least partially surrounding the absorbent porous material on at least two sides thereof, and having a bottom surface with an adhesive strip disposed thereon; and
   a vacuum assembly coupled to the proximal tube end of the tube channel and operably configured to induce negative pressure within the tube channel and the bifurcated tube channel, the at least two bifurcated tube portions defining an open space between outer surfaces of the absorbent porous material surrounding each of the at least two bifurcated tube portions and spanning from the joint of the at least two bifurcated tube portions for flanking a target irrigation area on a user's skin, the open space disposed for receiving ambient liquid over the target irrigation area thereby causing, with the induced negative pressure within the tube channel and the bifurcated tube channel by the vacuum assembly, ambient fluid absorption through the plurality of apertures and into the tube channel and the bifurcated tube channel.

2. The suction-based dressing assembly according to claim 1, wherein:
   the occlusive sheet material on each of the at least two bifurcated tube portions at least partially surround three sides of the absorbent porous material.

3. The suction-based dressing assembly according to claim 2, wherein:
   the occlusive sheet material is adhesively coupled to the absorbent porous material on the three sides thereof to form a U-shaped channel shaped and sized to receive the absorbent porous material, wherein the absorbent porous material is gauze.

4. The suction-based dressing assembly according to claim 2, wherein the at least two bifurcated tube portions each further comprise:
   a first end directly coupled together to define the joint interposed between the proximal tube end of the flexible tube and the distal tube end of each of the at least two bifurcated tube portions; and
   a bifurcated tube length separating the joint and the distal tube end, the U-shaped channel of the occlusive sheet material spanning at least 50% of the bifurcated tube length.

5. The suction-based dressing assembly according to claim 4, wherein:
   the U-shaped channel of the occlusive sheet material spans at least 75% of the bifurcated tube length and is of a polymeric material.

6. The suction-based dressing assembly according to claim 4, wherein:
   the adhesive strip is of a polymeric material and spans an occlusive sheet material length separating the entire U-shaped channel.

7. The suction-based dressing assembly according to claim 1, wherein:
   the distal tube end defines a distal tube opening fluidly coupled to the bifurcated tube channel.

8. The suction-based dressing assembly according to claim 1, wherein:
   the bifurcated portion of the flexible tube is of an oblong shape.

9. The suction-based dressing assembly according to claim 1, wherein:
   the at least two bifurcated tube portions each further comprise:
      a first end directly coupled together to define a joint interposed between the proximal tube end of the flexible tube and the distal tube end of each of the least two bifurcated tube portions; and
      a bifurcated tube length separating the joint and the distal tube end, the occlusive sheet material spanning at least 50% of the bifurcated tube length.

10. The suction-based dressing assembly according to claim 9, wherein the occlusive sheet further comprises:
    a bottom wall portion including the bottom surface and an inner surface;
    a sidewall portion directly coupled to the bottom wall portion to form a continuously watertight joint and including an inner surface; and
    an upper wall portion directly coupled to the sidewall portion and including an inner surface, the inner surfaces of the bottom wall portion, the sidewall portion, and the upper wall portion surrounding at least 50% of a circumference defined by the absorbent porous material spanning at least 50% of the bifurcated tube length.

11. The suction-based dressing assembly according to claim 1, wherein:
the bifurcated tube channel fluidly couples to the tube channel at a joint.

12. The suction-based dressing assembly according to claim 1, wherein:
the vacuum assembly comprises a vacuum pump inducing pressure between 5 to 12 pounds per square inch.

13. A suction-based dressing assembly comprising:
a flexible tube:
defining a tube channel and having a proximal tube end defining a proximal tube opening fluidly coupled to the tube channel; and
including a distal tube end and defining a plurality of apertures thereon fluidly coupled to the tube channel;
an absorbent porous material surrounding the plurality of apertures;
an occlusive sheet material having a bottom wall portion with a bottom surface, a sidewall portion directly coupled to the bottom wall portion, and an upper wall portion directly coupled to the sidewall portion to collectively serve as a watertight joint to prevent fluid from seeping therethrough and forming a U-shaped channel exposing the absorbent porous material thereon to an ambient environment and partially surrounding the absorbent porous material only with the bottom wall portion, the sidewall portion, and the upper wall portion, the bottom surface of the occlusive sheet material with an adhesive strip disposed thereon and spanning an occlusive sheet material length, the adhesive strip being operable to adhere to a user's skin, the flexible tube operably configured to be flexed and adhered to the user's skin with the adhesive strip on the occlusive sheet material and with the exposed absorbent porous material to flank a target irrigation area on the user's skin and define an open space between outer surfaces of the exposed absorbent porous material;
a vacuum assembly coupled to the proximal tube end of the tube channel and operably configured to induce negative pressure within the tube channel causing ambient fluid absorption through the plurality of apertures and into the tube channel; and
whereby the fluid is operably configured to be drawn from the open space between outer surfaces of the exposed absorbent porous material and on the user's skin, through the exposed absorbent porous material, and through the tube channel for discharge through the proximal tube opening.

14. The suction-based dressing assembly according to claim 13, further comprising:
a bifurcated portion on the flexible tube with at least two bifurcated tube portions each defining a bifurcated tube channel fluidly coupled to the tube channel, having a distal end located thereon, and defining the plurality of apertures fluidly coupled to each respective bifurcated tube channel, the absorbent porous material surrounding the plurality of apertures on one of the at least two bifurcated tube portions, an absorbent porous material surrounding the plurality of apertures on another of the at least two bifurcated tube portions, and separate pieces of occlusive sheet material, each with the bottom wall portion, the sidewall portion, and the upper wall portion coupled the respective the respective absorbent porous material.

15. The suction-based dressing assembly according to claim 14, wherein:
the occlusive sheet material is adhesively coupled to the absorbent porous material on the three sides thereof to form a U-shaped channel shaped and sized to receive the absorbent porous material.

16. The suction-based dressing assembly according to claim 13, wherein:
the adhesive strip comprises a polymeric material, the adhesive strip separating the entire U-shaped channel.

17. The suction-based dressing assembly according to claim 13, wherein:
the at least two bifurcated tube portions each further comprise:
a first end directly coupled together to define a joint interposed between the proximal tube end of the flexible tube and the distal tube end of each of the least two bifurcated tube portions; and
a bifurcated tube length separating the joint and the distal tube end, the occlusive sheet material spanning at least 50% of the bifurcated tube length.

18. The suction-based dressing assembly according to claim 17, wherein:
the occlusive sheet further comprises:
the bottom wall portion including the bottom surface and an inner surface;
the sidewall portion directly coupled to the bottom wall portion to form a continuously watertight joint and including an inner surface; and
the upper wall portion directly coupled to the sidewall portion and including an inner surface, the inner surfaces of the bottom wall portion, the sidewall portion, and the upper wall portion surrounding at least 50% of a circumference defined by the absorbent porous material spanning at least 50% of the bifurcated tube length.

19. The suction-based dressing assembly according to claim 17, wherein:
the bifurcated tube channel fluidly couples to the tube channel at a joint.

20. A method of dermal irrigation with suction-based dressing assembly, comprising:
applying a dermal irrigation procedure to a target irrigation area of the skin;
connecting a vacuum assembly to a proximal tube end of a tube, the tube being in fluid communication with at least two bifurcated tube portions having a plurality of apertures;
covering a substantial length of the bifurcated tube portions with an absorbent gauze material;
at least partially surrounding the absorbent gauze material on at least two sides with an occlusive sheet material to expose the absorbent porous material to an ambient environment, the occlusive sheet material having an adhesive strip on a bottom surface;
adhering the adhesive strip of the occlusive sheet material to the skin at or near the target irrigation area to define an open space between outer surfaces of the exposed absorbent material with the target irrigation area of the skin between the open space between outer surfaces of the exposed absorbent material;
actuating the vacuum assembly to induce negative pressure within the tube and the bifurcated tube;
absorbing, through the exposed absorbent gauze material, ambient fluid residue from the dermal irrigation;
sucking the ambient fluid through the apertures in the bifurcated tube, whereby the negative pressure causes the ambient fluid to absorb through the absorbent gauze material, the plurality of apertures, and into the bifurcated tube; and discharging the ambient fluid through a proximal tube opening in the proximal tube end of the tube.

\* \* \* \* \*